United States Patent [19]

Kuehne

[11] 4,154,943

[45] May 15, 1979

[54] PREPARATION OF VINCADIFFORMINE

[75] Inventor: Martin E. Kuehne, Burlington, Vt.

[73] Assignee: University of Vermont, Burlington, Vt.

[21] Appl. No.: 865,657

[22] Filed: Dec. 29, 1977

[51] Int. Cl.$^2$ ............................................ C07D 487/16
[52] U.S. Cl. ............................. 546/51; 260/326.14 R; 546/85
[58] Field of Search ...... 260/287 P, 239 BE, 239 BF; 546/51

[56] References Cited

FOREIGN PATENT DOCUMENTS 811614  7/1974  Belgium.

OTHER PUBLICATIONS

Kutney et al., "Journal of the American Chemical Society", 90:14 (Jul.) 1968.
Laronze et al., "Tetrahedron Letters", No. 6, pp. 491-494 (1974).
Stork et al., J.A.C.S., 85:2872 (1963).
Ziegler et al., J.A.C.S., 92:11 (1970).
Ando et al., J.A.C.S., 97:23 (1975), 6880-6881.
Buchi et al., J.A.C.S., 93:13 (1971), 3299-3301.
Ziegler et al., "J.A.C.S.", 93:22 (1971), 5930-5931.
Kan-Fan et al., "J.C.S. Chem. Comm.", (1974), pp. 164-165.
Ban et al., "Tetrahedron Letters," 49, pp. 5027-5030 (1972).
Mason et al., "Chem. Comm.", 915 (1967).
Scott et al., "Tetrahedron Letters, " vol. 30, pp. 2993-3002 (1974).

*Primary Examiner*—Donald G. Daus
*Assistant Examiner*—David E. Wheeler
*Attorney, Agent, or Firm*—Pollock, Vande Sande & Priddy

[57] ABSTRACT

The invention relates to the preparation of vincadifformine.

Tetrahydro-$\beta$-carboline (II) is reacted with benzoyl chloride to provide 2-benzoyl-1,2,3,4-tetrahydro-9H-pyrido-[3,4b]-indole (III). Then compound (III) is reduced to give 2-benzyl-1,2,3,4-tetrahydro-9H-pyrido[3,4b]-indole (IV). Thereafter, compound (IV) is transformed by t-butyl hypochlorite into chloroindolenine derivative (V) which is immediately treated with thallium t-butyl methyl malonate to give t-butyl methyl 3-benzyl-1,2,3,4,5,6-hexahydroazepino-[4,5b]-indole-5,5-dicarboxylate (VI). Compound (VI) is then partly decarboxylated into methyl 3-benzyl-1,2,3,4,5,6-hexahydroazepino-[4,5b]-indole-5-carboxylate (VII). Compound (VII) is hydrogenated to give methyl 1,2,3,4,5,6-hexahydroazepino-[4,5b]-indole-5-carboxylate (IX). In an alternative embodiment, compound (VI) can be hydrogenated to methyl t-butyl 1,2,3,4,5,6-hexahydroazepino-[4,5b]-indole-5,5-dicarboxylate (VIII) which is then decarboxylated into compound (IX). Compound (IX) is condensed with 1-bromo-4-formylhexane to yield vincadifformine (I).

15 Claims, No Drawings

PREPARATION OF VINCADIFFORMINE

The invention described herein was made in the course of work under a grant or award from the Department of Health, Education, and Welfare.

The present invention relates to a synthesis process for vincadifformine and to the intermediates produced in the process.

Vincadifformine is an alkaloid which constitutes raw material for preparing alkaloids of the vincamine group as in the processes described in the U.S. Pat. Nos. 3,892,755, and 3,894,028 and Belgian Pat. Nos. 772.005 and 848.475.

Two methods of total synthesis of vincadifformine are already described in the literature by J. Kutney, Ka Kong Chan, Ame Failli, J. M. Fromson, C. Gletsos et V. R. Nelson, J.A.C.S., 90, 3891 (1968) et J. Y. Laronze, J. Laronze et Fontaine, J. Levy et J. Le Men, Tetrahedron Letters, 491 (1974).

The object of the present invention is a new preparation process for vincadifformine through a total synthesis with higher yield and which does not require reagents which cannot be used in large quantities.

A further object of the invention is the obtention of new intermediates involved in the vincadifformine synthesis as set forth herein.

The steps involved in the synthesis of vincadifformine and the various intermediates are set forth in the accompanying drawing.

In the above-indicated formulae Φ represents a phenyl ring.

The invention can be distinguished more particularly by the fact that in a first step the tetrahydro-β-carboline (II) when treated with benzoyl chloride yields 2-benzoyl-1,2,3,4,-tetrahydro-9H-pyrido-[3,4b]-indole (III).

In a second step, the reduction of III by lithium aluminum hydride (LAH) in tetrahydrofuran (THF) yields the 2-benzyl-1,2,3,4-tetrahydro-9H-pyrido [3,4b] indole (IV).

In a third step, derivative IV is transformed by the action of tert.-butyl hypochlorite into chloroindolenine (V) which is immediately treated with thallium t-butyl methyl malonate giving t-butyl methyl 3-benzyl-1,2,3,4,5,6-hexahydroazepino-[4,5b]-indole-5,5-dicarboxylate (VI).

In a fourth step, derivative VI is partly decarboxylated by means of trifluoroacetic anhydride or trifluoroacetic acid into methyl 3-benzyl-1,2,3,4,5,6-hexahydroazepino-[4,5b]-indole-5-carboxylate (VII).

In a fifth step, product VII is hydrogenated in the presence of Pd/C at 5% giving methyl 1,2,3,4,5,6-hexahydroazepino-[4,5b]-indole-5-carboxylate (IX).

In an alternative of the invention, product VI can be hydrogenated in presence of Pd/C at 5% to yield methyl t-butyl 1,2,3,4,5,6-hexahydroazepino-[4,5b]-indole-5,5-dicarboxylate (VIII) which is then decarboxylated into IX.

In a sixth step, product IX is condensed with 1-bromo-4-formyl-hexane to yield vincadifformine (I) through temporary formation of intermediate compound (X) of the formula:

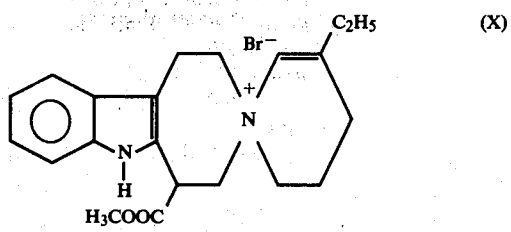

The compound 1-bromo-4-formyl-hexane is prepared by acetalisation of either methyl 4-formyl-hexanoate or ethyl 4-formyl-hexanoate to form methyl 4-dimethoxymethyl-hexanoate or ethyl 4-diethoxymethyl-hexanoate respectively, reduction by lithium hydride into 4-dimethoxy-methyl-1-hexanol or 4-diethoxy-methyl-1-hexanol respectively, dehydroxy bromination of the alcohol thus forming either 1-bromo-4-dimethoxymethyl-1-hexane or 1-bromo-4-diethoxymethyl-hexane respectively followed by the hydrolysis thereof to form the desired 1-bromo-4-formyl-hexane.

The following examples set forth in a non limitative way the characteristics of the invention.

EXAMPLE 1

2-benzoyl-1,2,3,4-tetrahydro-9H-pyrido-[3,4b]-indole (III)

Tetrahydro-β-carboline (II) (3 g, 17.44 mmol) was suspended in dry benzene (50 ml) and pyridine (20 ml). Benzoyl chloride (3 ml, 25.8 mmol) was added dropwise, with stirring at room temperature. After addition was complete the mixture was heated at 70° C. for 1 hour.

The hot mixture was then poured into 200 ml of water and the layers separated. The water layer was washed with benzene (2×50 ml) and the combined organic phases were washed with water (2×25 ml), 1 N HCl (2×20 ml), water (20 ml) and (sat) sodium bicarbonate (2×20 ml).

The solvent was evaporated and the residual brown oil dissolved in 10 ml of benzene. Hexane (60 ml) was slowly added with scratching to induce crystallization. Pure benzoylated amine was obtained (4.57 g, 95%). Recrystallization from aqueous ethanol gave white needles.

mp: 156°-157° C.

IR (CHCl$_3$): 3470, 3060, 3020, 2925, 2860, 1625, 1620, 1575, 1490, 1460, 1435, 1305, 1205, 1150, 1045, 1025, 980 cm$^{-1}$.

NMR (CDCl$_3$) δ 2.80 (bs, 2 H), 3.65 (bs, 2 H), 4.80 (bs, 2 H) 7.0–7.30 (m, 9 H), 8.75 (bs, 1 H).

Mass spectrum (80 eV) m/e (rel intensity) 276 (M+, 8), 262 (16), 168 (15), 143 (100), 105 (15), 91 (21), 77 (16), 44 (44), 40 (71).

Analysis calculated for C$_{18}$H$_{16}$N$_2$O: C, 78.24; H, 5.84; N, 10.14. Found: C, 78.24; H, 5.92; N, 10.18.

EXAMPLE 2

2-benzoyl-1,2,3,4-tetrahydro-9H-pyrido-[3,4b]-indole (IV)

To a solution of lithium aluminum hydride (1 g, 26.3 mmol) in 100 ml of dry THF at room temperature was added a solution of N-benzoyltetrahydro-β-carboline (III) (4.5 g, 16.3 mmol) in 100 ml of dry THF over 15 min.

The stirred solution was refluxed for 10 hours, then cooled to room temperature.

Water (1 ml) was added dropwise, followed by 15% aqueous NaOH (1 ml) and water (3 ml) and the solution stirred vigorously for 30 min.

The granular precipitate was filtered and washed several times with ether. The filtrate and washings were dried over sodium sulfate.

Filtration and evaporation of solvent produced white solid (4.26 g, 99.5%).

mp: 140°–141° C. lit. mp 142° C. see (a) M. Onda and M. Samamoto, Pharm. Bull (Tokyo), 5, 305 (1957), (b) M. Protiva, Z. J. Vedjdelek, J. O. Jilek and K. Macek, Coll. Czech. Chem. Comm. 24, 3978 (1959).

NMR (CDCl$_3$) δ 2.80 (bs, 4 H), 3.45 (s, 2 H), 3.65 (s, 2 H) 6.92–7.40 (m, 9 H), 7.48 (bs, 1 H).

Mass spectrum (80 eV) m/e (rel intensity) 262 M+, 19), 261 (5), 144 (24), 143 (100), 142 (4), 91 (19), 40 (21).

EXAMPLE 3 t-butyl methyl 3-benzyl-1,2,3,4,5,6-hexahydroazepino-[4,5b]-indole-5,5-dicarboxylate (VI)

The chloroindolenine (V) was prepared by dissolving the N-benzyl amine (IV) (3.522 g, 13.44 mmol) in 100 ml of dry benzene and cooling to 5° C.

To the cold stirring solution was added dry triethylamine (1.16 g, 10 mmol, 1.6 ml) followed by dropwise addition of t-butyl hypochlorite (1.458 g, 13.44 mmol, 1.6 ml).

The reaction was kept in an ice bath for 1.5 hour, then poured into water at 0° C. (20 ml).

The benzene layer was separated and dried over sodium sulfate. The solution was filtered and the volume reduced to one half by vacuum evaporation. Dry benzene was added to a total volume of ca. 100 ml, then thallium t-butyl methyl malonate (5.28 g, 14 mmol) was added and the stirred solution refluxed for 36 hours. The reaction was cooled to room temperature and filtered through glass fiber paper. The solvent was removed and the residue adsorbed onto silica gel (20 g, Woelm Act III for dry column chromatography). The adsorbed material was placed on top of a 6"×1.5" column of the dry column silica gel and eluted with dichloromethane.

The first 20 ml was discarded and the product was collected in the next 150 ml (3.69 g, 63.3%) recrystallized from aqueous methanol.

mp: 118°–120° C.

IR (CHCl$_3$): 3460, 3440, 3080, 3050, 3020, 2995, 2975, 2940, 2820, 1730, 1610, 1445, 1365, 1250, 1150, 1025, 840, 695 cm$^{-1}$.

NMR (CDCl$_3$) δ 1.44 (s, 9 H), 2.82 (bs, 4 H), 3.60 (s, 2 H), 3.66 (s, 3 H), 3.76 (s, 2 H), 6.84–7.4 (m, 9 H), 8.36 (bs, 1 H).

Mass spectrum (80 eV) m/e (rel intensity) 434 (7), 334 (30), 216 (57), 156 (57), 91 (68), 59 (78), 56 (76), 44 (81), 41 (78), 40 (100).

Analysis calculated for $C_{26}H_{30}N_2O_4$: C, 71.86; H, 6.96; N, 6.45. Found: C, 71.97; H, 7.03; N, 6.16.

EXAMPLE 4 methyl 3-benzyl-1,2,3,4,5,6-hexahydroazepino-[4,5b]-indole-5-carboxylate (VII)

The t-butyl ester (VI) (1.890 g, 4.35 mmol) was dissolved in 80 ml of 1,2-dichloroethane and the system flushed with nitrogen. Anhydrous trifluoroacetic acid (1.6 ml) was added via syringe through a rubber septum.

The solution was stirred at reflux for 3.5 hours. The hot reaction mixture was poured into 100 ml of cold (sat) aqueous sodium carbonate. The layers were separated and the aqueous phase extracted with 50 ml of dichloroethane. The combined organic phases were washed with (sat) sodium carbonate solution and filtered through phase separating paper onto anhydrous potassium carbonate. Filtration and evaporation of the solvent produced a brown oil which was triturated with ethyl-acetate-heptane to induce crystallization.

The offwhite solid was collected in two crops to yield 1.219 g (84%) of desired decarboxylated amine of formula VII. The compound was recrystallized twice from aqueous ethanol for analysis.

mp: 135°–135.5° C.

IR (CHCl$_3$): 3480, 3075, 3045, 2940, 2840, 1740, 1600, 1500, 1460, 1435, 1350, 1275, 1230, 1220, 1200, 1163, 1026 cm$^{-1}$.

NMR (CDCl$_3$) δ 2.94 (bs, 4 H), 3.24 (m, 2 H), 3.76 (s, 3 H), 3.88 (s, 2 H), 4.16 (m, 1 H), 6.97–7.7 (m, 9 H), 8.68 (bs, 1 H).

Mass spectrum (80 eV) m/e (rel intensity) 334 (M+, 37), 216 (100), 156 (61), 91 (49), 42 (32).

Analysis calculated for $C_{21}H_{22}N_2O_2$: C, 75.42; H, 6.63; N, 8.38. Found: C, 75.63; H, 6.90; N, 8.41.

EXAMPLE 5 methyl t-butyl 1,2,3,4,5,6-hexahydroazepino-[4,5b]-indole-5,5-dicarboxylate (VIII)

A solution of N-benzyl amine (VI) (202 mg, 0.465 mmol) in dry acetic acid (7.5 ml) was hydrogenated under 1 atm. pressure hydrogen with 5% Pd/C catalyst (22 mg) for 1.5 hour.

The catalyst was filtered and washed with hot methanol.

The solvent was removed from the filtrate by evaporation leaving a light yellow oil which was dissolved in dichloromethane (50 ml). The solution was cooled to 0° C., 10% aqueous NaOH (25 ml) added, and the solution stirred vigorously for 10 min.

The organic phase was separated and dried over anhydrous potassium carbonate. The solution was filtered and the solvent evaporated to a light yellow oil which resisted all attempts at crystallization but was the desired pure debenzylated diester-amine (155 mg, 97%) of formula VIII.

IR (CHCl$_3$): 3445, 3435, 3035, 2975, 2915, 1730, 1615, 1455, 1430, 1365, 1250, 1140, 1020, 840, 800 cm$^{-1}$.

NMR (CDCl$_3$) δ 1.48 (s, 9 H), 2.24 (s, 1 H), 2.96 (m, 2 H), 3.16 (m, 2 H), 3.72 (m, 2 H), 3.78 (s, 3 H), 7.04–7.60 (m, 4 H), 8.88 (bs, 1 H).

Mass spectrum (80 eV) m/e (rel intensity) 344 (M+, 100%), 245 (82), 229 (56), 216 (96), 215 (87), 203 (87), 171 (67), 155 (74).

EXAMPLE 6 methyl 1,2,3,4,5,6-hexahydroazepino-[4,5b]-indole-5-carboxylate (IX)

The monoester-benzylamine (VII) of example 4 (915 mg, 2.74 mmol) was dissolved in 50 ml of glacial acetic acid and 100 mg of 5% Pd/C catalyst added. The mixture was hydrogenated under 1 atm pressure for 18 hours, then filtered through glass fiber paper.

The catalyst was washed with 50 ml of hot methanol and the combined filtrates were evaporated to an oily residue. The residue was dissolved in 75 ml of chloroform and 100 ml of saturated aqueous sodium carbonate were added. The two phase system was stirred vigorously for 15 min. and the layers then separated. The aqueous phase was washed with chloroform and the combined chloroform phases were washed with brine, then filtered through phase separating paper onto anhydrous potassium carbonate. The material was filtered and the solvent evaporated leaving a thick oily residue which was solidified by trituration with ethyl acetate heptane. The material was filtered yielding 532 mg (80%) of desired debenzylated amine (IX).

The mother liquor was chromatographed on silica gel with dichloromethane as eluent, producing another 87 mg of desired material for a combined yield of 93%. The material can be recrystallized from ethyl acetate-heptane.

mp: 138°–139° C.

IR (CHCl$_3$): 3465, 2950, 2925, 1735, 1630, 1460, 1435, 1220, 1160, 1015 cm$^{-1}$.

NMR (CDCl$_3$) δ 2.20 (bs, 4 H), 8.48 (bs, 1 H).

Mass spectrum (80 eV) m/e (rel intensity) 244 (M$^+$, 58), 215 (29), 202 (100), 170 (31), 156 (26), 142 (35), 43 (80), 42 (30).

EXAMPLE 7

(±) vincadifformine (I)

Method 1:

The bromo-aldehyde 1-bromo-4-formyl hexane (194.5 mg, 1 mmol) was dissolved in 6 ml of dry methanol under a nitrogen atmosphere and 123 mg (0.50 mmol) of amine IX was added in 6 ml of methanol. The mixture was stirred at room temperature for 1 hour, then dry triethylamine (0.5 ml) was added and the solution warmed to 40° C. for 12 hours. The reaction was cooled to room temperature and the solvent evaporated. The residue was taken up in CH$_2$Cl$_2$ (40 ml) and extracted with (sat) aqueous sodium carbonate (10 ml). The organic layer was dried over anhydrous potassium carbonate and filtered. The solvent was evaporated and the residue spotted on a preparative TLC plate (2 mm, Merck alumina) and developed with dichloromethane. The band at R$_f$0.4–0.6 was eluted, resulting in 71 mg of pure (±) vincadifformine as a white solid. The alkaloid was recrystallized from 95% ethanol.

mp: 124°–125° C. (lit. 124°–125° C. see J. Kutney, K. Chan, A. Failli, J. M. Fromson, C. Gletsus and V. Nelson, J. Am. Chem. Soc., 90, 3891 (1968)).

IR (CHCl$_3$): 3420, 3360, 2930, 2850, 2775, 1665, 1605, 1470, 1460, 1432, 1290, 1275, 1250, 1235, 1155, 1110, 1045 cm$^{-1}$.

NMR (CDCl$_3$) δ 1.6–3.6 (complex m, 18 H), 3.76 (s, 3 H), 6.74–7.5 (m, 4 H), 8.96 (bs, 1 H).

UV (EtOH) nm (log ε) 225 (4.12), 297 (3.15), 327 (4.06).

Mass spectrum (80 eV) m/e (rel intensity) 338 (M$^+$, 67), 124 (100).

Method 2:

The amine IX (125.8 mg, 0.515 mmol) was dissolved in dry benzene (3 ml) and 1-bromo-4-formyl hexane (97.5 mg, 0.505 mmol) was added. The mixture was stirred at 45° C. for 51 hours then dissolved in ether-dichloromethane (1:4). The solution was extracted with 1.0 N HCl and the aqueous phase washed with benzene. The aqueous layer was adjusted to pH 11–12 with 10% aqueous sodium hydroxide and extracted with chloroform. After drying and concentration, a light yellow oil remained (90 mg) which was separated by PTLC (Merck alumina, 5% methanol/95% dichloromethane). The band of R$_f$0.5–0.7 was isolated and eluted yielding (±) vincadifformine (45 mg, 26%) as an oil which crystallized upon seeding.

Examples 8–12 hereafter disclose the preparation of intermediate compounds for use in the preparation of 1-bromo-4-formyl-hexane, one of the reactants used in example 7.

EXAMPLE 8 methyl 4-dimethoxymethyl-hexanoate

To a solution containing anhydrous methanol (70 ml) and concentrated sulfuric acid (3 drops) was added methyl 4-formylhexanoate (10.2 g, 64.5 mmol). The solution was stirred at room temperature for 24 hours then solid potassium carbonate was added to neutralize the acid. Most of the solvent was evaporated under vacuum then water (100 ml) was added and the solution extracted twice with hexane (50 ml) then twice ether. The organic phases were combined and dried over anhydrous magnesium sulfate.

The solvent was evaporated under vacuum yielding the desired acetal with no aldehyde contamination (12.27 g, 93.2%).

bp: 60°–70° C. (Kugelrohr, 0.1 mm).

IR (neat): 2950, 2820, 1730, 1430, 1170, 1105, 1070, 960, 885 cm$^{-1}$.

NMR (CDCl$_3$) δ 0.88 (t, 3 H), 1.24–1.96 (m, 5 H), 2.34 (t, 2 H), 3.32 (s, 6 H), 3.82 (s, 3 H), 4.10 (d, 1 H).

Mass spectrum (80 eV) m/e (rel intensity) 204 (M$^+$, 1), 203 (6), 173 (100), 141 (99), 109 (73), 99 (90), 75 (97).

EXAMPLE 9 ethyl 4-diethoxymethyl-hexanoate

The ethyl acetal was prepared from the aldehyde in 84% yield in the same manner as the methyl acetal. The ester group exchanges under these conditions.

bp: 90°–100° C. (Kugelrohr, 0.1 mm).

NMR (CDCl$_3$) δ 0.95 (t, 3 H), 1.23 (t, 6 H), 1.33 (t, 3 H), 1.25–2.06 (m, 5 H), 2.43 (t, 2 H), 3.63 (q, 4 H) 4.23 (q, 2 H), 4.40 (d, 1 H).

EXAMPLE 10

4-dimethoxymethyl-1-hexanol

The methyl acetal ester (9.8 g, 48 mmol) end product of example 8 was dissolved in THF (tetrahydrofurane) (20 ml) and added dropwise at 0° C. to an ether solution of LAH (lithiumaluminum hydride) (50 ml of 1 M solution). After addition was completed (ca. 30 min.) the reaction was allowed to warm to room temperature and water (1 ml) was added slowly. Enough 20% aqueous KOH was added to dissolve the solid and the solution extracted five times with ether (25 ml). The ether extracts were washed with brine and dried over anhydrous sodium sulfate. Evaporation of the solvent yielded the desired alcohol (7.86 g, 93%) as a clear colorless liquid.

IR (neat): 3400, 2940, 2830, 1460, 1380, 1190, 1110, 1060, 960 cm$^{-1}$.

NMR (CDCl$_3$) δ 0.9 (t, 3 H), 1.4 (m, 7 H), 2.9 (bs, 1 H), 3.2 (s, 6 H), 3.42 (t, 2 H), 4.15 (d, 1 H).

EXAMPLE 11

4-diethoxymethyl-1-hexanol

A solution of the ethyl acetal-ester (9.367 g, 38 mmol) end product of example 9 in THF (40 ml) was added to 0° C. to a solution of LAH in ether (40 ml of 1 M solution) over 0.5 hour. The reaction was refluxed 1 hour then allowed to cool to room temperature. Magnesium sulfate heptahydrate (9.86 g, 40 mmol) was added and the reaction stirred vigorously 12 hours. The solid was filtered and washed with ether several times. The combined filtrate and washings were washed with 10% aqueous KOH (10 ml) then brine (10 ml) and dried over anhydrous sodium sulfate. Evaporation of the solvent followed by Kugelrohr distillation (bp 90°-100° C., 0.1 mm) produced the hydroxy-acetal (7.0 g, 90.3%).

IR (neat): 3400, 2985, 2940, 1880, 1460, 1380, 1115, 1065, 730 cm$^{-1}$.

NMR (CDCl$_3$) δ 0.93 (t, 3 H), 1.23 (t, 6 H), 1.16–1.83 (m, 7 H) 2.16 (bs, 1 H), 3.66 (m, 6 H), 4.40 (d, 1 H).

EXAMPLE 12

1-bromo-4-dimethoxymethyl-hexane

Carbon tetrabromide (1.824 g, 5.5. mmol) and triphenylphosphine (1.443 g, 5.5 mmol) in ether (15 ml) were refluxed 0.5 hour then cooled to room temperature. The 4-dimethoxymethyl-1-hexanol in ether (6 ml) was added dropwise resulting in rapid decolorization of the yellow slurry and precipitation of a buff colored solid. The mixture was filtered through Celite and the solvent removed inder vacuum. The residue was placed under high vacuum (ca. 10$^{-3}$ mm) to remove the excess carbon tetrabromide and the bromoform by-product. The distillation pot was heated to 50°-60° C. and the distillate collected with the aid of a dry-ice trap. The distillate was the desired bromo-acetal (700 mg, 66%) contaminated with a trace of carbon tetrabromide and bromoform. This compound was used without further purification for hydrolysis.

Hydrolysis of the product of example 12 (bromo-acetal or 4-dimethoxymethyl-1-bromohexane) to the corresponding bromo-aldehyde (1-bromo-4-formyl-hexane) was achieved by stirring in THF/1 N HCl (10:1) (6 ml) at room temperature for 24 hours (94% yield).

For comparison, the bromo-acetal was prepared from the bromo-aldehyde. The bromo-aldehyde (52.4 mg, 0.27 mmol) was dissolved in dry methanol (1 ml) and one crystal of p-toluenesulfonic acid was added. The solution was stirred at room temperature for 48 hours then poured into dichloromethane (15 ml). The solution was washed with sat aqueous sodium carbonate (5 ml) and dried over anhydrous sodium sulfate. Concentration yielded the acetal (60.4 mg, 93.2%) as a colorless oil with the following characteristics:

IR (neat): 2960, 1460, 1110, 1070 cm$^{-1}$.

NMR (CDCl$_3$) δ 0.92 (t, 3 H), 1.20–2.04 (m, 7 H), 3.38 (s, 6 H) 3.40 (t, 2 H), 4.16 (d, 1 H).

Mass spectrum (80 eV) m/e (rel intensity) 238, 240 (M+, 0.01), 207, 209, (38, 37), 75 (100).

What I claim is:

1. A process for the preparation of vincadifformine of the formula:

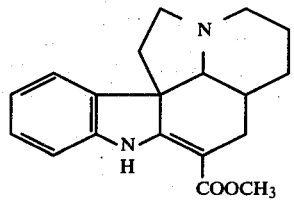

which comprises the steps of:
(a) reacting a tetrahydro-β-carboline of the formula:

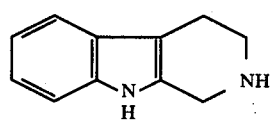

with benzoyl chloride to form a compound of the formula:

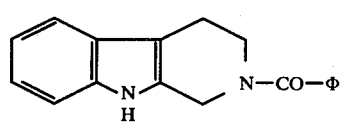

wherein Φ represents phenyl
(b) reducing the compound of formula III by means of a reducing agent to form a compound of the formula:

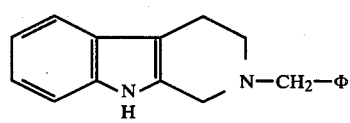

(c) chlorinating the compound of formula IV with t-butyl hypochlorite in the presence of triethylamine to form a compound of the formula:

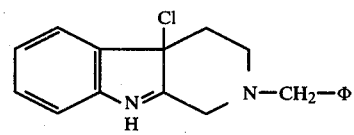

(d) reacting the compound of formula V with thallium t-butyl methyl malonate at reflux to form a compound of the formula:

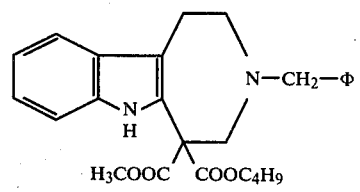

(e) decarboxylating partly the compound of formula VI at reflux and in the presence of a reagent selected from anhydrous trifluoroacetic acid and anhydrous trifluoroacetic anhydride and mixtures thereof to form a compound of the formula:

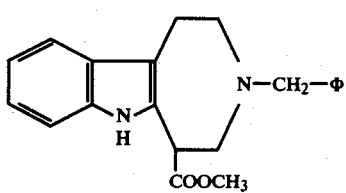
(VII)

(f) hydrogenating the compound of formula VII into a compound of the formula:

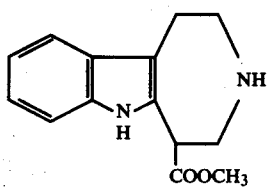
(IX)

(g) reacting the compound of formula IX with 1-bromo-4-formylhexane in the presence of the triethylamine to yield the desired vincadifformine of formula I.

2. A process for the preparation of vincadifformine of the formula:

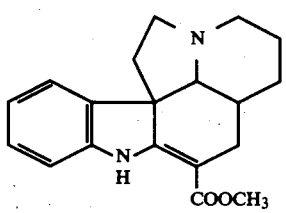
(I)

which comprises the steps of:
(a) reacting a tetrahydro-β-carboline of the formula:

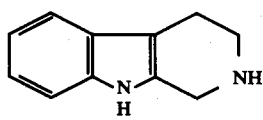
(II)

with benzoyl chloride to form a compound of the formula:

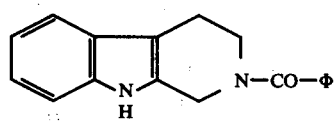
(III)

wherein Φ represents phenyl
(b) reducing the compound of formula III by means of a reducing agent to form a compound of the formula:

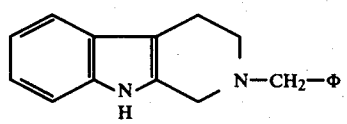
(IV)

(c) chlorinating the compound of formula IV with t-butyl hypochloride in the presence of triethylamine to form a compound of the formula:

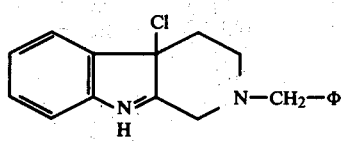
(V)

(d) reacting the compound of formula V with thallium t-butyl methyl malonate at reflux to form a compound of the formula:

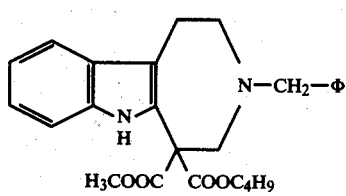
(VI)

(e) hydrogenating the compound of formula VI into a compound of the formula:

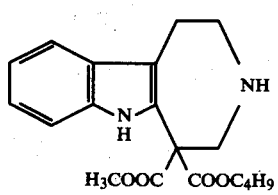
(VIII)

(f) decarboxylating partly the compound of formula VIII at reflux and in the presence of a reagent selected from anhydrous trifluoracetic acid and anhydrous trifluoracetic anhydride and mixtures thereof to form a compound of the formula:

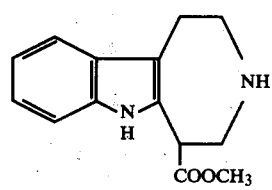
(IX)

(g) reacting the compound of formula IX with 1-bromo-4-formylhexane in the presence of triethylamine to yield the desired vincadifformine of formula I.

3. A process according to claim 1 wherein step a is effected by reacting tetrahydro-β-carboline (II) in dry benzene and pyridine, with benzoyl chloride at 70° C., thus providing N-benzoyltetrahydro-β-carboline of formula III which in step b is reduced by means of lithium aluminium hydride under reflux heating conditions giving 2-benzyl-1,2,3,4-tetrahydro-9H-pyrido-[3,4b]-indole of formula IV, the latter compound being in step c reacted with t-butyl hypochlorite under cooling in the presence of dry triethylamine to form the chloroindolenine of formula V which in step d, following immediately after step c, is reacted with thallium t-butyl methyl malonate under reflux heating conditions to give the t-butyl methyl 3-benzyl-1,2,3,4,5,6-hexahydroazepino-[4,5b]-indole-5,5-dicarboxylate of formula VI which then undergoes steps e up to g to form the desired vincadifformine of formula I.

4. A process according to claim 2, wherein the t-butyl methyl 3-benzyl-1,2,3,4,5,6-hexahydroazepino-[4,5b]- indole-5,5-dicarboxylate of formula VI as obtained in step d is according to step e hydrogenated in dry acetic acid under 1 atm. pressure of hydrogen with 5% Pd/C catalyst to form methyl t-butyl 1,2,3,4,5,6-hexahydroazepino-[4,5b]-indole-5,5-dicarboxylate of formula VIII which then in step f is treated with a compound selected from the group consisting of anhydrous trifluoracetic acid and anhydrous trifluoracetic anhydride under reflux heating and nitrogen blanket conditions to provide the methyl 1,2,3,4,5,6-hexahydroazepino-[4,5b]-indole-5-carboxylate of formula IX, the latter compound being in step g transformed into the desired vincadifformine of formula I.

5. A process according to claim 1, wherein the t-butyl methyl 3-benzyl-1,2,3,4,5,6-hexahydroazepino [4,5b]-indole-5,5-dicarboxylate of formula VI as obtained in step d is according to step e treated in a 1,2-dichloroethane medium with a compound selected from the group consisting of anhydrous acetic acid and trifluoracetic acid, anhydrous trifluoracetic anhydride, and mixtures thereof under reflux heating and nitrogen blanket conditions to provide the methyl 3-benzyl-1,2,3,4,5,6-hexahydroazepino-[4,5b]-indole-5-carboxylate of formula VII which in step f is hydrogenated in glacial acetic acid medium with a 5% Pd/C catalyst under 1 atm. pressure to provide the methyl 1,2,3,4,5,6-hexahydroazepino-[4,5b]-indole-5-carboxylate of formula IX, the latter compound then being in step g transformed into the desired vincadifformine of formula I.

6. A process according to claim 1, wherein the methyl 1,2,3,4,5,6-hexahydroazepino-[4,5b]-indole-5-carboxylate of formula IX as obtained in step f is reacted according to step g with 1-bromo-4-formyl-hexane in dry methanol under a nitrogen blanket in the presence of dry triethylamine at room temperature to provide the desired vincadifformine of formula I.

7. A process according to claim 1, wherein the methyl 1,2,3,4,5,6-hexahydroazepino-[4,5b] indole-5-carboxylate of formula IX as obtained in step f is reacted according to step g with 1-bromo-4-formyl-hexane in dry benzene at 45° C. to provide the desired vincadifformine of formula I.

8. A process according to claim 7, wherein 1-bromo-4-formyl-hexane as used in step g results from a process including the following steps of
(A) acetalisation of a $C_1$-$C_2$ alkyl 4-formyl-hexanoate to provide a corresponding alkyl 4-dialkoxymethylhexanoate.
(B) reduction of the compound of step A into a corresponding 4-dialkoxy-methyl-1-hexanol
(C) dehydroxy bromination of the compound of step B into a corresponding 1-bromo-4-dialkoxymethylhexane
(D) hydrolysis of the compound of step C to form the desired 1-bromo-4-formyl-hexane.

9. A process according to claim 8 wherein in step A the alkyl 4-formyl-hexanoate is reacted with the corresponding anhydrous $C_1$-$C_2$ alkanol at room temperature in step B the compound of step A is reduced by means of lithium-aluminium hydride in step C bromination of the compound of step B is effected by means of carbon tetrabromide at room temperature, and in step D hydrolysis of the compound of step C is effected by means of hydrochloric acid at room temperature.

10. The process of claim 1 wherein said reducing agent employed in step (b) is lithium aluminum hydride.

11. The process of claim 1 wherein the hydrogenating in step (f) is carried out in the presence of a Pd catalyst.

12. The process of claim 9 wherein said bromination is carried out in the presence of triphenylphosphine.

13. A process for preparing t-butyl methyl 3-benzyl-1,2,3,4,5,6-hexahydroazepino-[4,5b]-indole-5,5-dicarboxylate of the formula:

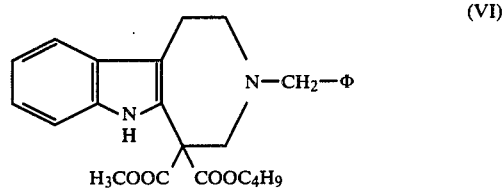

(VI)

which comprises the step of chlorinating 2-benzyl-1,2,3,4-tetrahydro-9H-pyrido [3,4b]-indole of the formula:

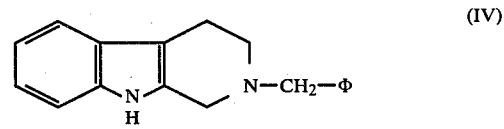

(IV)

with t-butyl hypochlorite under cooling in the presence of dry triethylamine to form a chloroindolenine of the formula:

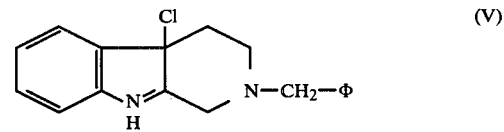

(V)

and immediately reacting said chloroindolenine (formula V) with thallium t-butyl methyl malonate under reflux heating conditions to provide the said dicarboxylate.

14. A process for preparing vincadifformine of the formula:

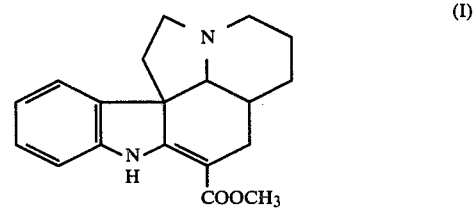

(I)

which comprises the step of reacting methyl 1,2,3,4,5,6-hexahydroazepino-[4,5b]-indole-5-carboxylate of the formula:

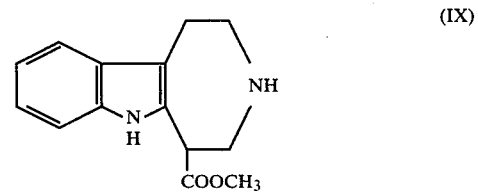

(IX)

with 1-bromo-4-formyl-hexane in dry methanol under a nitrogen atmosphere in the presence of dry triethylamine at room temperature to yield vincadifformine (I) through temporary formation of intermediate compound (X) of the formula:

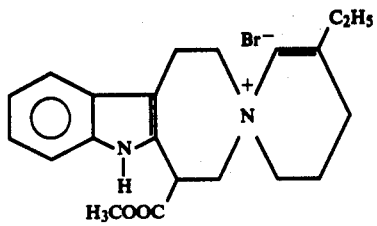
15. A process for preparing vincadifformine of the formula:
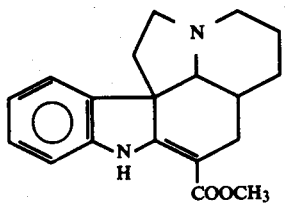
which comprises the step of reacting methyl 1,2,3,4,5,6-hexahydroazepino-[4,5b]-indole-5-carboxylate of the formula:
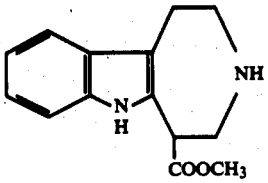
with 1-bromo-4-formyl-hexane in dry benzene under heating to yield vincadifformine (I) through temporary formation of intermediate compound (X) of the formula:
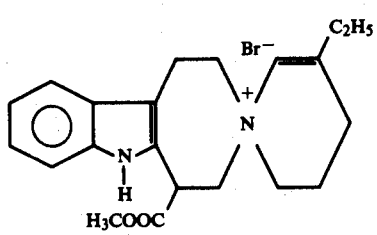
* * * * *